US010328148B2

(12) United States Patent
Topp et al.

(10) Patent No.: US 10,328,148 B2
(45) Date of Patent: Jun. 25, 2019

(54) PROTEIN DRUG FORMULATIONS AND PACKAGES

(71) Applicant: Purdue Research Foundation, West Lafayette, IN (US)

(72) Inventors: Elizabeth Murphy Topp, Lafayette, IN (US); Frederick E. Regnier, West Lafayette, IN (US); Jun Zhang, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 472 days.

(21) Appl. No.: 15/061,866

(22) Filed: Mar. 4, 2016

(65) Prior Publication Data
US 2016/0206735 A1 Jul. 21, 2016

Related U.S. Application Data

(63) Continuation of application No. 13/642,333, filed as application No. PCT/US2011/033620 on Apr. 22, 2011, now abandoned.

(60) Provisional application No. 61/327,371, filed on Apr. 23, 2010.

(51) Int. Cl.
| *A61K 39/395* | (2006.01) |
| *C07K 16/00* | (2006.01) |
| *C07K 16/12* | (2006.01) |
| *C07K 7/08* | (2006.01) |
| *C07K 14/31* | (2006.01) |
| *A61K 47/64* | (2017.01) |
| *A61K 39/00* | (2006.01) |

(52) U.S. Cl.
CPC ...... *A61K 39/39591* (2013.01); *A61K 47/641* (2017.08); *A61K 47/645* (2017.08); *C07K 7/08* (2013.01); *C07K 14/31* (2013.01); *C07K 16/00* (2013.01); *C07K 16/1282* (2013.01); *A61K 2039/505* (2013.01); *C07K 2317/94* (2013.01)

(58) Field of Classification Search
None
See application file for complete search history.

(56) References Cited

U.S. PATENT DOCUMENTS

| 4,699,783 A * | 10/1987 | Terman ............... A61K 35/16 424/178.1 |
| 5,429,746 A | 7/1995 | Shadle et al. |
| 6,013,763 A * | 1/2000 | Braisted ............... C07K 14/31 436/828 |
| 2005/0143566 A1 | 6/2005 | Hober |
| 2008/0102073 A1 | 5/2008 | Koff |

FOREIGN PATENT DOCUMENTS

| WO | WO-8904675 A1 * | 6/1989 | ......... A61M 1/3679 |
| WO | WO9204381 | 3/1992 | |

OTHER PUBLICATIONS

Jiang et al., J Chromatogr A. Jul. 31, 2009;1216(31):5849-55. doi: 10.1016/j.chroma.2009.06.013. Epub Jun. 10, 2009.*
Godfrey et al., "Assessment of the suitability of commercially available SpA affinity solid phases for the purification of murine monoclonal antibodies at precess scale", Journal of Immunological Methods, vol. 160, 1993, 9 pages.
Jena Bioscience, "Protein A Agarose" Data Sheet, 2009, 2 pages.
Office action for U.S. Appl. No. 13/642,333, dated Nov. 4, 2015, Topp et al., "Protein Drug Formulations and Packages", 10 pages.
Office Action for U.S. Appl. No. 13/642,333, dated Apr. 1, 2015, Topp et al., "Protein Drug Formulations and Packages", 8 pages.
Pan et al., "Methionine oxidation in human IgG2Fc decreases binding affinities to protein A and FcRn", Protein Science, vol. 18, Dec. 2008, pp. 424-433.
PCT Search Report & Written Opinion for Application No. PCT/GB91/01554, dated Jan. 22, 1992, 73 pages.
PCT Search Report & Written Opinion for Application No. PCT/US2011/33620, dated Oct. 17, 2011, 12 pages.
Pierce, "Optimize elution conditions for immunoaffinity purification", available at <<www.piercenet.com>>, 2004, 2 pages.
Wang et al., "Antibody Structure, Instability, and Formulation", in the Journal of Pharmaceutical Sciences, vol. 96, No. 1, Jan. 2007, 26 pages.

* cited by examiner

*Primary Examiner* — Michael Szperka
(74) *Attorney, Agent, or Firm* — Purdue Research Foundation; Yonghao Hou

(57) ABSTRACT

Compositions and methods that include stabilized protein drugs are described. In addition, protein drug formulations that are more stable under ambient conditions are described. The formulations include one or more poly amino acid ligands of the protein drug.

20 Claims, 2 Drawing Sheets

Specification includes a Sequence Listing.

SEQUENCE LISTING

```
<160> NUMBER OF SEQ ID NOS: 16

<210> SEQ ID NO 1
<211> LENGTH: 21
<212> TYPE: PRT
<213> ORGANISM: Staphylococcus aureus
<220> FEATURE:
<221> NAME/KEY: MISC_FEATURE
<222> LOCATION: (4)...(18)
<223> OTHER INFORMATION: Xaa can be naturally occurring amino acid or a
      derivative thereof

<400> SEQUENCE: 1

Phe Asn Lys Xaa Ala Ala Gln Gln Xaa Ala Ala Ala Phe Tyr Xaa Ala
1               5                   10                  15

Ala Xaa Ala Ala Leu
            20

<210> SEQ ID NO 2
<211> LENGTH: 14
<212> TYPE: PRT
<213> ORGANISM: Staphylococcus aureus
<220> FEATURE:
<221> NAME/KEY: MISC_FEATURE
<222> LOCATION: (1)
<223> OTHER INFORMATION: Xaa can be any naturally occurring amino acids
      or derivatives thereof

<400> SEQUENCE: 2

Xaa Ala Ala Gln Arg Asn Gly Phe Ile Gln Ser Leu Lys Asp
1               5                   10

<210> SEQ ID NO 3
<211> LENGTH: 13
<212> TYPE: PRT
<213> ORGANISM: Staphylococcus aureus

<400> SEQUENCE: 3

Phe Asn Lys Glu Gln Gln Asn Ala Phe Tyr Glu Ile Leu
1               5                   10

<210> SEQ ID NO 4
<211> LENGTH: 12
<212> TYPE: PRT
<213> ORGANISM: Staphylococcus aureus

<400> SEQUENCE: 4

Glu Gln Arg Asn Gly Phe Ile Gln Ser Leu Lys Asp
1               5                   10

<210> SEQ ID NO 5
<211> LENGTH: 17
<212> TYPE: PRT
```

<213> ORGANISM: Staphylococcus aureus

<400> SEQUENCE: 5

Thr Val Thr Glu Lys Val Ile Asp Ala Ser Glu Leu Thr Pro Ala Val
1               5                   10                  15

Thr

<210> SEQ ID NO 6
<211> LENGTH: 9
<212> TYPE: PRT
<213> ORGANISM: Staphylococcus aureus

<400> SEQUENCE: 6

Cys Ala Gln Cys His Thr Val Glu Lys
1               5

<210> SEQ ID NO 7
<211> LENGTH: 9
<212> TYPE: PRT
<213> ORGANISM: Staphylococcus aureus

<400> SEQUENCE: 7

Gly Ala Gln Gly His Val Val Glu Lys
1               5

<210> SEQ ID NO 8
<211> LENGTH: 6
<212> TYPE: PRT
<213> ORGANISM: Staphylococcus aureus

<400> SEQUENCE: 8

His Trp Arg Gly Trp Val
1               5

<210> SEQ ID NO 9
<211> LENGTH: 6
<212> TYPE: PRT
<213> ORGANISM: Staphylococcus aureus

<400> SEQUENCE: 9

His Tyr Phe Lys Phe Asp
1               5

<210> SEQ ID NO 10
<211> LENGTH: 6
<212> TYPE: PRT
<213> ORGANISM: Staphylococcus aureus

<400> SEQUENCE: 10

His Phe Arg Arg His Leu
1               5

<210> SEQ ID NO 11
<211> LENGTH: 18
<212> TYPE: PRT
<213> ORGANISM: Staphylococcus aureus

<400> SEQUENCE: 11

Thr Val Thr Glu Lys Pro Glu Val Ile Asp Ala Ser Trp Leu Pro Ala
1               5                   10                  15

Val Thr

<210> SEQ ID NO 12

```
<211> LENGTH: 8
<212> TYPE: PRT
<213> ORGANISM: Staphylococcus aureus

<400> SEQUENCE: 12

Thr Val Thr Glu Lys Pro Glu Val
1               5

<210> SEQ ID NO 13
<211> LENGTH: 9
<212> TYPE: PRT
<213> ORGANISM: Staphylococcus aureus

<400> SEQUENCE: 13

Gly Ala Gln Gly His Thr Val Glu Lys
1               5

<210> SEQ ID NO 14
<211> LENGTH: 11
<212> TYPE: PRT
<213> ORGANISM: Staphylococcus aureus

<400> SEQUENCE: 14

Cys Gln Asn Trp Ile Lys Asp Val His Lys Cys
1               5                   10

<210> SEQ ID NO 15
<211> LENGTH: 11
<212> TYPE: PRT
<213> ORGANISM: Staphylococcus aureus

<400> SEQUENCE: 15

Cys His Lys Arg Ser Phe Trp Ala Asp Asn Cys
1               5                   10

<210> SEQ ID NO 16
<211> LENGTH: 11
<212> TYPE: PRT
<213> ORGANISM: Staphylococcus aureus

<400> SEQUENCE: 16

Cys Arg Thr Gln Phe Arg Pro Asn Gln Thr Cys
1               5                   10
```

PROTEIN DRUG FORMULATIONS AND PACKAGES

CROSS-REFERENCE TO RELATED APPLICATIONS

This application is a continuation of, and claims priority to and the benefit of, U.S. patent application Ser. No. 13/642,333, filed Oct. 19, 2012, which is a 35 USC § 371 filing of International Application No. PCT/2011/033620, filed Apr. 22, 2011, which claims priority to and the benefit of U.S. Provisional Patent Application Ser. No. 61/327,371, filed Apr. 23, 2010, the entirety of each of which is incorporated herein by reference.

STATEMENT OF FEDERALLY SPONSORED RESEARCH OR DEVELOPMENT

This invention was made with Government support under Contract No. R01GM085293 awarded by the National Institutes of Health. The government has certain rights in the invention.

TECHNICAL FIELD

Examples described herein pertain to compositions and methods that include stabilized protein drugs. In particular, examples described herein pertain to protein drug formulations that are more stable under ambient conditions

BACKGROUND

Protein drugs are believed to be one of the fastest growing sectors of the pharmaceutical industry, but development is often hindered by the inherent instability of these large, complex molecules. Protein drugs having an Fc domain are particularly useful in treating diseases. However, it has been reported that protein drugs having an Fc domain exhibit low stability, because among other things, such protein drugs reportedly homodimerize or aggregate, adopt non-active or less active conformations, and/or denature by unfolding, partially unfolding, or improperly refolding. It has also been reported that such protein drug stability may occur during storage, and/or is accelerated by agitation, especially at temperatures at or above ambient. Accordingly, such protein drugs are stored at refrigerated temperatures, and a cold-chain is reportedly required to be maintained from the point of manufacture to the point of administration.

Particularly in the case of underdeveloped countries, such as Sub-Saharan Africa and Latin America, protein drugs in the form of vaccines have been an important tool in the arsenal of combating diseases. However, many of those protein formulations including vaccines must be kept refrigerated in order to maintain the stability of the drugs during storage or transportation until administered. Not surprisingly, in many those countries most in need of such protein drugs, the availability of electricity is either sporadic or non-existent, making refrigeration of the drugs unreliable or not possible. Protein drugs must be formulated to preserve stability during manufacturing, shipping and storage so that a safe and fully potent drug is administered to the patient. Administering a partially degraded protein drug may increase the risk for life-threatening side effects, particularly if protein aggregates are present. Current stabilization strategies include adding excipients, refrigerating the product, or producing a dried form. However, for a given protein, the appropriate stabilizing strategy is typically identified by trial-and-error and by experience, a process that can take years at considerable cost. An inability to stabilize a protein may preclude commercialization, so that a promising drug is lost to the market and to the patients who need it. It is therefore understood that a need exists for protein drug formulations, and storage that is less susceptible to these and other limitations.

It has also been reported that protein drugs may have insufficiently long in vivo half-life for optimal treatment efficacy. Covalent modification of protein drugs, that includes covalent addition of polyethylene glycols, also referred to as PEGylation, has been reported as a possible solution to the observed short half-life (see, for example, PEGylation of therapeutic proteins in Biotechnol J 5:113-128 (2010)). It is therefore understood that a need also exists for protein drug formulations that exhibit longer in vivo half-life, including protein drug formulations that do not require a covalent modification of the protein drug.

It has been discovered that proteins having an Fc domain exhibit higher stability when mixed with one or more of the polyamino acid ligands described herein. It has also been discovered herein that protein drugs are stabilized by binding to polyamino acid ligands. It is to be understood that as used herein, polyamino acid ligands includes peptide ligands of varying lengths, such as oligopeptide ligands and polypeptide ligands, and also includes protein ligands. Without being bound by theory, it is believed herein that such mixtures of proteins having an Fc domain and the polyamino acid ligands described herein form complexes that may stabilize the active conformation, decrease the denaturation, and/or decrease the homodimerization or aggregation of the proteins having the Fc domain. Without being bound by theory, it is also believed herein that one possible mechanism of decreasing aggregation of the protein having an Fc domain is due to the creation of a steric barrier upon formation of the complex. The steric barrier may generally or indirectly decrease or prevent the homodimerization or aggregation by crowding the sites of interaction that would be used by the proteins having an Fc domain to form homodimers or aggregates. Without being bound by theory, it is also believed herein that one possible mechanism of decreasing aggregation of the protein having an Fc domain is due to a competitive interaction between the one or more ligands and the region of the protein having an Fc domain that initiates, stabilizes, and/or forms the dimer or aggregate. The competitive interaction may generally or directly decrease or prevent the homodimerization or aggregation by competitively blocking the sites of interaction that would be used by the proteins having an Fc domain to form homodimers or aggregates. Without being bound by theory, it is also believed herein that one possible mechanism of decreasing aggregation of the protein having an Fc domain is due to the separation in space of complexes in configurations of the complexes that are attached to a solid support.

Described herein are methods for stabilizing protein drugs using one or more polyamino acid ligands as binding agents. These methods exploit the large and structurally diverse pool of natural ligands to develop new stabilizing materials for protein drugs, and are believed to have more general applicability to a wide variety of protein drugs.

In one embodiment, pharmaceutical compositions that include a drug comprising a protein having an Fc domain, and one or more polyamino acid ligands for the protein are described herein. In another embodiment, the composition is a solution. In another embodiment, the composition is a suspension. In another embodiment, the composition is a solid, such as a solid prepared from a solution and/or suspension described herein. The solid may be reconstituted to prepare a solution and/or suspension described herein. In another embodiment, the composition includes a solid support comprising the one or more polyamino acid ligands covalently attached thereto.

In another embodiment, the compositions may be used as a means of storage of the drug comprising a protein having an Fc domain. In another embodiment, the compositions may be administered as a drug composition. In another embodiment, the protein having an Fc domain is released or separated from the one or more polyamino acid ligands prior to administration.

DETAILED DESCRIPTION

Figure 1:
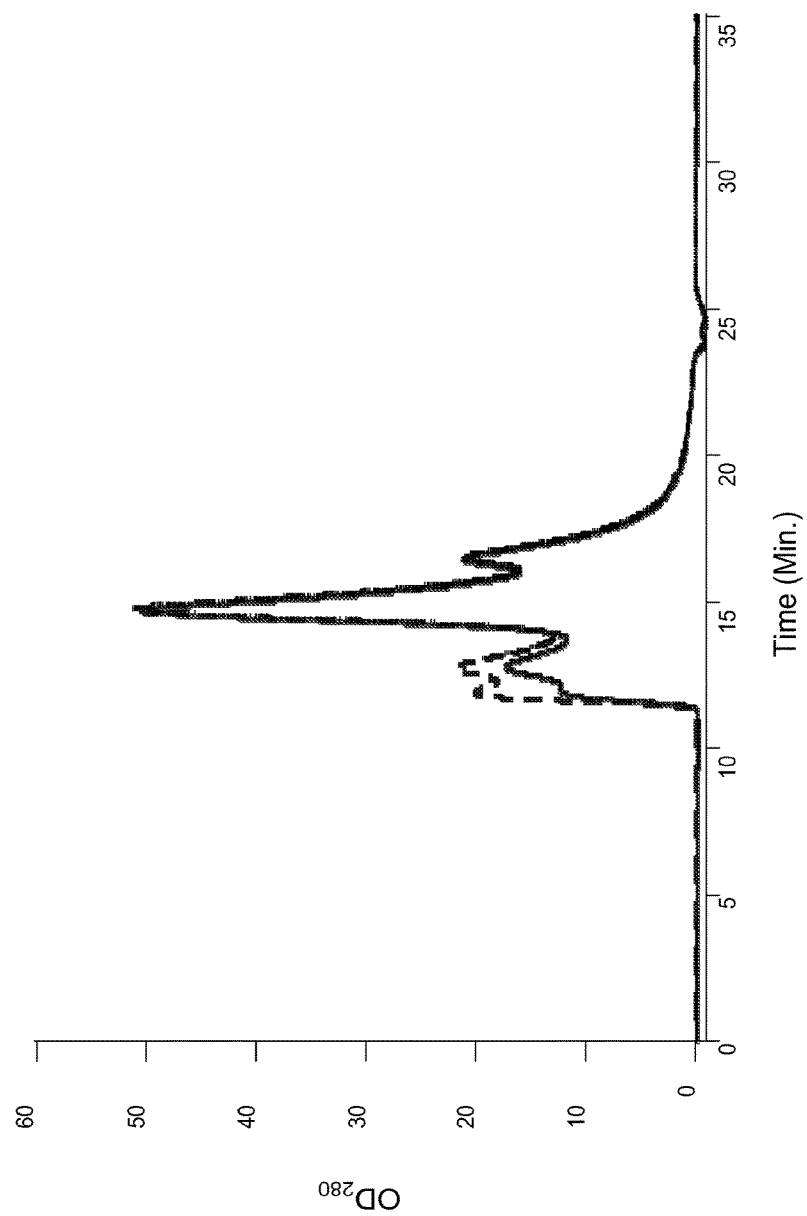
FIG. 1 shows a comparison between the mixture of IgG and Protein A stored at ambient temperature for 44 h (solid line), and the same mixture agitated for 44 h at ambient temperature (dashed line).

In another embodiment, described herein is a pharmaceutical composition comprising a protein drug, where the protein drug includes an Fc domain; and one or more polyamino acid ligands for the protein.

In another embodiment, described herein is the composition as in any of the preceding embodiments wherein the protein is an immunoglobulin.

In another embodiment, described herein is the composition as in any of the preceding embodiments wherein the protein is an immunoglobulin G or immunoglobulin G-like protein.

In another embodiment, described herein is the composition as in any of the preceding embodiments wherein the protein is IgG1.

In another embodiment, described herein is the composition as in any of the preceding embodiments wherein the protein is IgG2.

In another embodiment, described herein is the composition as in any of the preceding embodiments wherein the protein is a human protein or a derivative thereof, including fusion proteins of human proteins, and the like.

In another embodiment, described herein is the composition as in any of the preceding embodiments wherein at least one ligand comprises an immunoglobulin-binding protein.

In another embodiment, described herein is the composition as in any of the preceding embodiments wherein at least one ligand comprises protein A, or a fragment thereof, or an analog or derivative of any of the foregoing.

In another embodiment, described herein is the composition as in any of the preceding embodiments wherein at least one ligand comprises protein G, or a fragment thereof, or an analog or derivative of any of the foregoing.

In another embodiment, described herein is the composition as in any of the preceding embodiments wherein at least one ligand comprises protein A, or a fragment thereof.

In another embodiment, described herein is the composition as in any of the preceding embodiments wherein at least one ligand comprises protein G, or a fragment thereof.

In another embodiment, described herein is the composition as in any of the preceding embodiments wherein at least one ligand comprises protein A/G, or a fragment thereof.

In another embodiment, described herein is the composition as in any of the preceding embodiments wherein at least one ligand is protein A.

In another embodiment, described herein is the composition as in any of the preceding embodiments wherein at least one ligand comprises domain B of protein A.

In another embodiment, described herein is the composition as in any of the preceding embodiments wherein at least one ligand is protein G.

In another embodiment, described herein is the composition as in any of the preceding embodiments wherein at least one ligand comprises domain II of protein G.

In another embodiment, described herein is the composition as in any of the preceding embodiments wherein at least one ligand comprises the peptide FNKXQQ-X1AFYX2X3L (SEQ ID NO: 1) where X, X1, X2, and X3 are naturally occurring amino acids or derivatives thereof.

In another embodiment, described herein is the composition as in any of the preceding embodiments wherein at least one ligand comprises the peptide X4QRNGFIQSLKD (SEQ ID NO: 2), where X4 is a naturally occurring amino acid or a derivative thereof.

In another embodiment, described herein is the composition as in any of the preceding embodiments wherein at least one ligand comprises the peptide FNKXQQ-X1AFYX2X3L (SEQ ID NO: 1) and the peptide X4QRNGFIQSLKD (SEQ ID NO: 2), where X, X1, X2, X3, and X4 are naturally occurring amino acids or derivatives thereof.

In another embodiment, described herein is the composition as in any of the preceding embodiments wherein FNKXQQX1AFYX2X3L (SEQ ID NO: 1) and X4QRN-GFIQSLKD (SEQ ID NO: 2) are covalently attached through a linking peptide, where X, X1, X2, X3, and X4 are naturally occurring amino acids or derivatives thereof.

In another embodiment, described herein is the composition as in any of the preceding embodiments wherein FNKXQQX1AFYX2X3L (SEQ ID NO: 1) and X4QRN-GFIQSLKD (SEQ ID NO: 2) are covalently attached through a linker, where X, X1, X2, X3, and X4 are naturally occurring amino acids or derivatives thereof.

In another embodiment, described herein is the composition as in any of the preceding embodiments wherein X1 is N or S.

In another embodiment, described herein is the composition as in any of the preceding embodiments wherein X2 is E or Q.

In another embodiment, described herein is the composition as in any of the preceding embodiments wherein X3 is I or V.

In another embodiment, described herein is the composition as in any of the preceding embodiments wherein X is E or D.

In another embodiment, described herein is the composition as in any of the preceding embodiments wherein X4 is E, D, or A.

In another embodiment, described herein is the composition as in any of the preceding embodiments wherein at least one ligand comprises the peptide FNKEQQNAFYEIL (SEQ ID NO: 3).

In another embodiment, described herein is the composition as in any of the preceding embodiments wherein at least one ligand comprises the peptide EQRNGFIQSLKD (SEQ ID NO: 4).

In another embodiment, described herein is the composition as in any of the preceding embodiments wherein at least one ligand comprises the peptide FNKEQQNAFYEIL (SEQ ID NO: 3) and the peptide EQRNGFIQSLKD (SEQ ID NO: 4).

In another embodiment, described herein is the composition as in any of the preceding embodiments wherein FNKEQQNAFYEIL (SEQ ID NO: 3) and EQRNGFIQSLKD (SEQ ID NO: 4) are covalently attached through a linking peptide.

In another embodiment, described herein is the composition as in any of the preceding embodiments wherein FNKEQQNAFYEIL (SEQ ID NO: 3) and EQRNGFIQSLKD (SEQ ID NO: 4) are covalently attached through a linker.

In another embodiment, described herein is the composition as in any of the preceding embodiments wherein the linking peptide comprises a polyaspartamide.

In another embodiment, described herein is the composition as in any of the preceding embodiments wherein the biodegradable polymer comprises a poly(alkylene oxide).

In another embodiment, described herein is the composition as in any of the preceding embodiments wherein the biodegradable polymer comprises a poly(ethylene oxide).

In another embodiment, described herein is the composition as in any of the preceding embodiments wherein at least one ligand includes an epitope for an antibody.

In another embodiment, described herein is the composition as in any of the preceding embodiments comprising two or more polyamino acid ligands for the protein.

In another embodiment, described herein is the composition as in any of the preceding embodiments wherein at least one ligand is capable of preserving the native or near-native conformation of the protein, preventing or minimizing unfolding of the protein, or preventing or minimizing aggregation of the protein, preventing or minimizing chemical degradation of the protein, or a combination thereof.

In another embodiment, described herein is the composition as in any of the preceding embodiments wherein at least one polyamino acid is a fragment of a receptor, where the receptor is capable of binding the protein.

In another embodiment, described herein is the composition as in any of the preceding embodiments wherein the ligand includes a coupling agent capable of being attached to the solid support.

In another embodiment, described herein is the composition as in any of the preceding embodiments wherein the ligand is attached to a solid support.

In another embodiment, described herein is the composition as in any of the preceding embodiments wherein the ligand is displaceable by a releasing agent of the protein to form a second composition capable of delivery to a patient.

In another embodiment, described herein is the composition as in any of the preceding embodiments wherein the releasing agent is glycine. It is to be understood that the releasing agent may be a competitive ligand for the polyamino acid ligand forming the protein drug mixture or protein drug complex. Such competitive ligands may be competitive, uncompetitive, or non-competitive, and may bind at or near the site of the competed polyamino acid ligand, or at any other site, including an allosteric site that will otherwise decrease, substantially decrease, or prevent the binding of any of the one or more polyamino acid ligands.

In another embodiment, described herein is the composition as in any of the preceding embodiments wherein the ligand is displaceable at acidic pH to form a second composition capable of delivery to a patient.

In another embodiment, described herein is the composition as in any of the preceding embodiments wherein the composition is in the form of dried solid.

In another embodiment, described herein is the composition as in any of the preceding embodiments wherein the composition is in the form of solution or suspension In another embodiment, described herein is the composition as in any of the preceding embodiments wherein the composition further comprises one or more carriers, diluents, or excipients, or combination thereof.

In another embodiment, described herein is a kit comprising a container and the composition as in any of the preceding embodiments; and a set of instructions for preparing a formulation for administering to a patient.

In another embodiment, described herein is a kit comprising a solid support, the composition as in any of the preceding embodiments, a releasing agent, and a set of instructions for preparing a formulation for administering to a patient; wherein the composition is attached to the support; and where the releasing agent is capable of removing the protein drug from the solid support when placed in contact with the composition attached to the solid support In another embodiment, described herein is the kit as in any of the preceding embodiments wherein the solid support is an amino modified glass.

In another embodiment, described herein is the kit as in any of the preceding embodiments wherein the solid support is a sterile glass vial suitable for preparing the formulation for administering to the patient.

In another embodiment, described herein is the kit as in any of the preceding embodiments wherein the solid support is a sterile glass syringe suitable for preparing the formulation for administering to the patient.

In another embodiment, described herein is the kit as in any of the preceding embodiments wherein the releasing agent comprises a glycine buffer.

In another embodiment, described herein is the kit as in any of the preceding embodiments wherein the releasing agent comprises protein A, or a fragment thereof.

In another embodiment, described herein is the kit as in any of the preceding embodiments wherein the releasing agent comprises a protein G, or a fragment thereof.

In another embodiment, described herein is the kit as in any of the preceding embodiments wherein the releasing agent comprises a protein A/G, or a fragment thereof.

In another embodiment, described herein is the kit as in any of the preceding embodiments wherein the releasing agent is an acid or an acidic buffer.

In another embodiment, described herein is a pharmaceutical composition comprising a drug comprising a protein, and one or more ligands for the protein. In another embodiment, described herein is a pharmaceutical formulation as mentioned above, comprising a drug comprising a protein, and two or more ligands for the protein. In one aspect, at least two of said ligands are different. In another aspect, at least one ligand comprises a peptide. In another aspect, at least two ligands each comprise a peptide. In another aspect, each ligand comprises a peptide.

In another embodiment, described herein is a pharmaceutical composition as described above, wherein each peptide includes 2 to about 50 amino acids, or derivatives thereof; or wherein each peptide includes 2 to about 15 amino acids, or derivatives thereof; or wherein each peptide includes about 5 to about 15 amino acids, or derivatives thereof.

In another embodiment, described herein is a pharmaceutical composition as described above, wherein at least one peptide is a dipeptide or tripeptide, or a derivative thereof.

In one aspect, at least one peptide is an epitope for an antibody. In another aspect, at least one peptide is a fragment of a receptor, where the receptor is capable of binding the protein.

In another embodiment, described herein is a pharmaceutical composition as described above, wherein at least one ligand is capable of preserving the native or near-native conformation of the protein, preventing or minimizing unfolding of the protein, and/or preventing or minimizing aggregation of the protein.

In another embodiment, described herein is a pharmaceutical composition as described above, wherein at least one ligand further comprises a biodegradable polymer.

In another embodiment, described herein is a pharmaceutical composition as described above, wherein at least two of the ligands are covalently attached to each other by a biodegradable polymer.

In another embodiment, described herein is a pharmaceutical composition as described above, wherein the polymer comprises a polypeptide.

In another embodiment, described herein is a pharmaceutical composition as described above, wherein the polymer comprises a naturally occurring protein or fragment thereof.

In another embodiment, described herein is a pharmaceutical composition as described above, wherein the polymer comprises a synthetic polymer.

In another embodiment, described herein is a pharmaceutical composition as described above, wherein the polymer comprises a polyaspartamide polymer.

In another embodiment, described herein is a pharmaceutical composition as described above, wherein the composition is biocompatible.

In another embodiment, described herein is a pharmaceutical composition as described above, wherein the composition is non-immunogenic.

In another embodiment, described herein is a pharmaceutical composition as described above, wherein the ligand is attached to a solid support.

In another embodiment, described herein is a pharmaceutical composition as described above, wherein the ligand includes a coupling agent capable of being attached to the solid support.

In another embodiment, described herein is a pharmaceutical composition as described above, wherein the ligand is displaceable by a competing ligand of the protein to form a second composition capable of delivery to a patient.

In another embodiment, described herein is a pharmaceutical composition as described above, wherein the composition is in the form of dried solid.

In another embodiment, described herein is a pharmaceutical composition as described above, wherein the composition is in the form of solution or suspension.

In another embodiment, described herein is a pharmaceutical composition as described above, wherein the composition further comprises one or more carriers, diluents, or excipients, or combination thereof.

In another embodiment, described herein is a pharmaceutical composition as described above, wherein the protein is an immunoglobulin. In another embodiment, the protein is Immunoglobulin G (IgG).

In another embodiment, described herein is a pharmaceutical composition as described above, wherein at least one ligand comprises an immunoglobulin-binding protein.

In another embodiment, described herein is a pharmaceutical composition as described above, wherein at least one ligand comprises protein A, or a fragment thereof. In another embodiment, described herein is a pharmaceutical composition as described above, wherein at least one ligand comprises protein G, or a fragment thereof. In another embodiment, described herein is a pharmaceutical composition as described above, wherein at least one ligand comprises protein A/G, or a fragment thereof.

In another embodiment, described herein is a kit comprising a container and a composition as described in any one of the preceding paragraphs; and a set of instructions for preparing a formulation for administering to a patient.

In another embodiment, described herein is a kit comprising a solid support, a composition as described in any one of the preceding paragraphs, a competing ligand, and a set of instructions for preparing a formulation for administering to a patient; wherein the composition is attached to the support, and the competing ligand is separately packaged; and where the competing ligand is capable of removing the protein drug from the solid support when placed in contact with the composition attached to the solid support. In one aspect, the solid support is an amino modified glass. In another aspect, the solid support is a sterile glass vial suitable for preparing the formulation for administering to the patient. In another aspect, the solid support is a sterile glass syringe suitable for preparing the formulation for administering to the patient.

In another embodiment, described herein is a kit as in the previous paragraph, wherein the competing ligand comprises a glycine buffer. In another embodiment, described herein is a kit as in the previous paragraph, wherein the competing ligand comprises protein A, or a fragment thereof. In another embodiment, described herein is a kit as in the previous paragraph, wherein the competing ligand comprises protein G, or a fragment thereof. In another embodiment, described herein is a kit as in the previous paragraph, wherein the competing ligand comprises protein A/G, or a fragment thereof.

Illustrative drug proteins having an Fc domain include, but are not limited to, immunoglobulins and immunoglobulin-like proteins, such as IgG, IgM, IgE, IgA, IgD, and the like, including analogs and derivatives thereof. It is to be understood that immunoglobulin-like proteins include various analogs and derivatives of immunoglobulins, such as fragments thereof, peptibodies, minibodies, immunoconjugates, immunotoxins, fusion proteins, antibody-targeted constructs and the like, and fragments of the foregoing. Illustratively, the proteins are immunoglobulin G proteins, such as human monoclonal IgG1, IgG2, IgG3, and IgG4, mouse monoclonal IgG1, IgG2a, IgG2b, and IgG3, rat monoclonal IgG1, IgG2a, IgG2b, and IgG2c, and the like. Illustratively, the proteins are immunoglobulin G-like proteins. Illustratively, the proteins are polyclonal immunoglobulins It is also to be understood that immunoglobulins and immunoglobulin-like proteins include both monoclonal and polyclonal variants. It is also to be understood that any source of the proteins having an Fc domain, such as natural sources and recombinant sources, are described herein.

Illustrative polyamino acid ligands include, but are not limited to, peptides and proteins that comprise one or more the polyamino acids TVTEKVIDASELTPAVT (SEQ ID NO: 5), CAQCHTVEK (SEQ ID NO: 6), GAQGHVVEK (SEQ ID NO: 7), HWRGWV (SEQ ID NO: 8), HYFKFD (SEQ ID NO: 9), HFRRHL (SEQ ID NO: 10), TVTEKPE-VIDASWLPAVT (SEQ ID NO: 11), TVTEKPEV (SEQ ID NO: 12), GAQGHTVEK (SEQ ID NO: 13), CQNWIKD-VHKC(SEQ ID NO: 14), CHKRSFWADNC(SEQ ID NO: 15), CRTQFRPNQTC(SEQ ID NO: 16), and the like, as described in Naik et al., Performance of hexamer peptide ligands for affinity purification of immunoglobulin G from commercial cell culture media, J Chromatography A 1218 (13):1691-1700 (2011); Jeong et al., Efficient selection of IgG Fc domain-binding peptides fused to fluorescent protein using E. coli expression system and dot-blotting assay, Peptides 31(2):202-206 (2010). Additional illustrative polyamino acid ligands are described in Roque et al., Affinity-based methodologies and ligands for antibody purification: Advances and perspectives, J Chromatography A, 1160(1-2):44-55 (2007); Li et al., Design, synthesis, and application of a Protein A mimetic, Nature Biotechnology 16(2):190-195 (1998); Huse et al., Purification of antibodies by affinity chromatography, J Biochem Biophys Methods 51(3):217-231 (2002); Deisenhofer, Crystallographic Refinement and Atomic Models of a Human Fc Fragment and its Complex with Fragment-B of Protein-A from *Staphylococcus-Aureus* at 2.9-A and 2.8-A Resolution, Biochemistry 20(9):2361-2370 (1981); Moks et al., Staphylococcal Protein-A Consists of 5 IgG-Binding Domains, Eur J Biochemistry 156(3):637-643 (1986); Langone, J. J., M. D. P. Boyle, and T. Borsos, Studies on Interaction Between Protein-A And Immunoglobulin-G.2. Composition and Activity of Complexes Formed Between Protein-A And IgG, J Immunology 121(1):333-338 (1978); Hanson & Schumaker, A Model for the Formation and Interconversion of Protein-A-Immunoglobulin-G Soluble Complexes, J Immunology 132(3):1397-1409 (1984); Guss et al., Structure Of The IgG-Binding Regions of Streptococcal Protein-G, Embo Journal 5(7):1567-1575 (1986); Olsson et al., Structure and Evolution of the Repetitive Gene Encoding Streptococcal Protein-G, Eur J Biochemistry 168(2):319-324 (1987); the disclosures of which are incorporated herein by reference.

In another embodiment, described herein is a method for stabilizing protein drugs in solution, in dried solids, and as immobilized on a solid support. The methods include one or more polyamino acid ligands of the protein drugs.

In another embodiment, described herein is the synthesis of a polyaspartamide polymers that are capable of being conjugated to the polyamino acid ligands described herein. It is to be understood that the polyamino acid ligands may be conjugated into the backbone of the polyaspartamide polymers and/or to one or more of the pendant carboxylic acid side chains. In another embodiment, the polyamino acid ligands are derived from protein G and/or protein A, and include fragments of those proteins. Without being bound by theory, it is believed that the flexible polypeptide backbone may allow in-line and/or pendant polyamino acids, epitopes, or other groups to bind to the protein drug, producing high binding affinity through multiple binding interactions.

It is to be understood that protein drug formulations described herein, and packages for protein drugs and formulations thereof may improve the ambient condition stability of the protein drug. Such stability improvement may include ambient temperature stability, agitation stability, and the like. It is appreciated herein that the embodiments where the mixture or complex of the protein drug and the one or more polyamino acids are administered to a patient, such polyamino acids are desirably or advantageously non-immunogenic. Illustratively, the polyaspartamide based polyamino acid ligands described herein may be non-immunogenic. Illustratively, the polyalkylene glyocol or poly-oxyalkylene based polyamino acid ligands described herein may be non-immunogenic. It is appreciated herein that the polyamino acid ligands are desirably biocompatible and/or non-immunogenic. In another embodiment, the polyamino acid ligands are biodegradable or metabolizable.

Many of the endogenous ligands for protein drugs are themselves peptides, polyamino acids, and/or proteins, whose structural diversity and multiple binding epitopes may produce specific binding interactions of very high affinity, and therefore may be used as the one of more polyamino acid ligands described herein.

In another embodiment, the polyamino acid ligands comprise fragments of the target receptor of the protein drug. It is to be understood that depending upon the nature of the target receptor, such embodiments of the polyamino acid ligands may include (a) one or more fragments of the primary sequence that forms at least a portion of the targeting interaction between the protein drug at the target receptor, or (b) a scaffold, including a peptide scaffold, that presents at least a portion of the residues that are included in the targeting interaction, where the residues are presented in an appropriate three dimensional arrangement that matches, minors, mimics, or approximates the arrangement found at the target receptor.

In another embodiment, peptide epitopes from a naturally occurring ligand, such as a receptor, of the protein drug are included in the compositions and methods described herein. Without being bound by theory, it is believed herein that such pseudo ligands may bind to the protein drug with high affinity, helping to preserve a near-native conformation.

Without being bound by theory, it is believed that preserving the structure of protein drugs minimizes unfolding and aggregation, such as my occur during manufacturing, shipping, and/or storage. Further, though without being bound by theory, it is also believed herein that such stabilization may also reduce chemical degradation. It is also believed that, when administered to the patient, the complex of the protein drug with the one or more ligands may provide increased circulating half-life, performing similar to but being a non-covalent alternative to PEGylated protein drugs.

In another embodiment, reagents, packages, and methods are described herein for immobilizing a protein drug onto a solid surface, where the solid surface has been modified by the covalent attachment of the one or more polyamino acid ligands described herein. Such covalent attachment of the one or more polyamino acid ligands to the solid surface may be accomplished using any conventional process or method. Illustrative methods include succinyl modification of the solid support, such as by the formation of succinate esters or succinamides thereof, and the like.

Illustrative solid supports include, but are not limited to glasses, such as Controlled Pore Glass (CPG) Long Chain Aminoalkyl Controlled Pore Glass (LCAA-CPG), and the like, plastics, such as macroporous polystyrene (MPPS), and the like, and other conventional solids, such as those that may be surface modified for attachment of the polyamino acid ligands described herein.

Without being bound by theory, it is also believed herein that complexes formed by the protein drugs and the one or more polyamino acid ligands may exhibit prolonged circulating half-life in vivo. It has been reported that covalent PEGylation of protein drugs increases circulating half-life in vivo. However, such covalent modification of the protein drug may be limited by a requirement that the PEGylation be removed to restore full activity of the protein drug at or near the target site or tissue, or alternatively, that the non-removable PEGylation does not impair the activity or efficacy of the protein drug. The mixtures and complexes described herein formed from protein drugs and polyamino acids are not covalent.

In another embodiment, storage formulations and packages are described herein. The storage formulations and packages also include protein drugs mixed with one or more polyamino acids; however, prior to use the protein drug is released from the polyamino acid complex. The released protein may also be administered in its free form. In another embodiment, the storage formulation is a solution formulation where the protein drug is released upon administering a releasing agent, such as an acid or a competing ligand that is capable of uncomplexing the protein drug from the one or more polyamino acid ligands. In another embodiment, the storage formulation is a dried solution formulation where the formulation is reconstituted into a solution and there after protein drug is released upon administering a releasing agent, such as an acid or a competing ligand that is capable of uncomplexing the protein drug from the one or more polyamino acid ligands. In another embodiment, the storage formulation is a solid support that is covalently attached to the one or more polyamino acid ligands, and the protein drug is released from the one or more polyamino acid ligands, and the covalently attached solid support, upon administering a releasing agent, such as an acid or a competing ligand that is capable of uncomplexing the protein drug from the one or more polyamino acid ligands.

In another embodiment, the solid support is included in a container suitable for performing the releasing step. In another embodiment, the solid support is itself a container that is configured or adapted to be covalently attached or allow covalent attachment of the one or more polyamino acid ligands.

It is to be understood that the pharmaceutical compositions described herein include an isolated complex of the proteins having an Fc domain and the one or more ligands. Accordingly, such complexes that form in vivo, or that form after the administration of separated configurations of the proteins having an Fc domain and/or the one or more ligands are not embodiments of the invention described herein.

EXAMPLES

The following examples further illustrate specific embodiments of the invention; however, the following examples should not be interpreted in any way to limit the invention.

The following abbreviations are used herein: ANOVA=analysis of variance, ATCC=American Type Culture Collection, Bis-ANS=4,4'-bis(1-anilinonaphthalene 8-sulfonate), Cy3=cyanine 3 (a water soluble fluorescent dye), Fmoc=9H-fluoren-9-ylmethoxycarbonyl, HP-SEC= high performance size exclusion chromatography, IEC=ion exchange chromatography, IgG=immunoglobulin G, MALDI=matrix-assisted laser desorption/ionization, MW=molecular weight, PAA=polyaspartamide, PEGylation= derivatization with polyethylene glycol (PEG), PSI=polysuccinimide, RH=relative humidity, RT=room/ambient temperature, SD=standard deviation, SDS-PAGE= sodium dodecyl sulfate polyacrylamide gel electrophoresis.

Example 1

Effect of proteins A and G on aggregation of IgG. High performance size exclusion chromatography (HP-SEC) is used to verify that IgG binds with Protein A or Protein G completely. 50 .mu.L aliquots are injected to a Tosoh TSK G 13000 SWXL Gel 3000 column (3000 mm.times.7.8 mm) and separated at a flow rate of 0.5 mL/min. The mobile phase contains 50 mM potassium phosphate and 100 mM K2SO4 at pH 7.1. The relative percentage of IgG monomer and dimer are calculated in triplicate as a percentage of the total chromatographic peak area at 280 nm. Fresh IgG is incubated with free Protein A or free Protein G, respectively, at IgG:Protein A or G ratio of 1:4 at RT for 2 h before being subjected to agitation. HP-SEC data demonstrate the formation of IgG-Protein A and IgG-Protein G complexes.

Example 2

Figure 2:
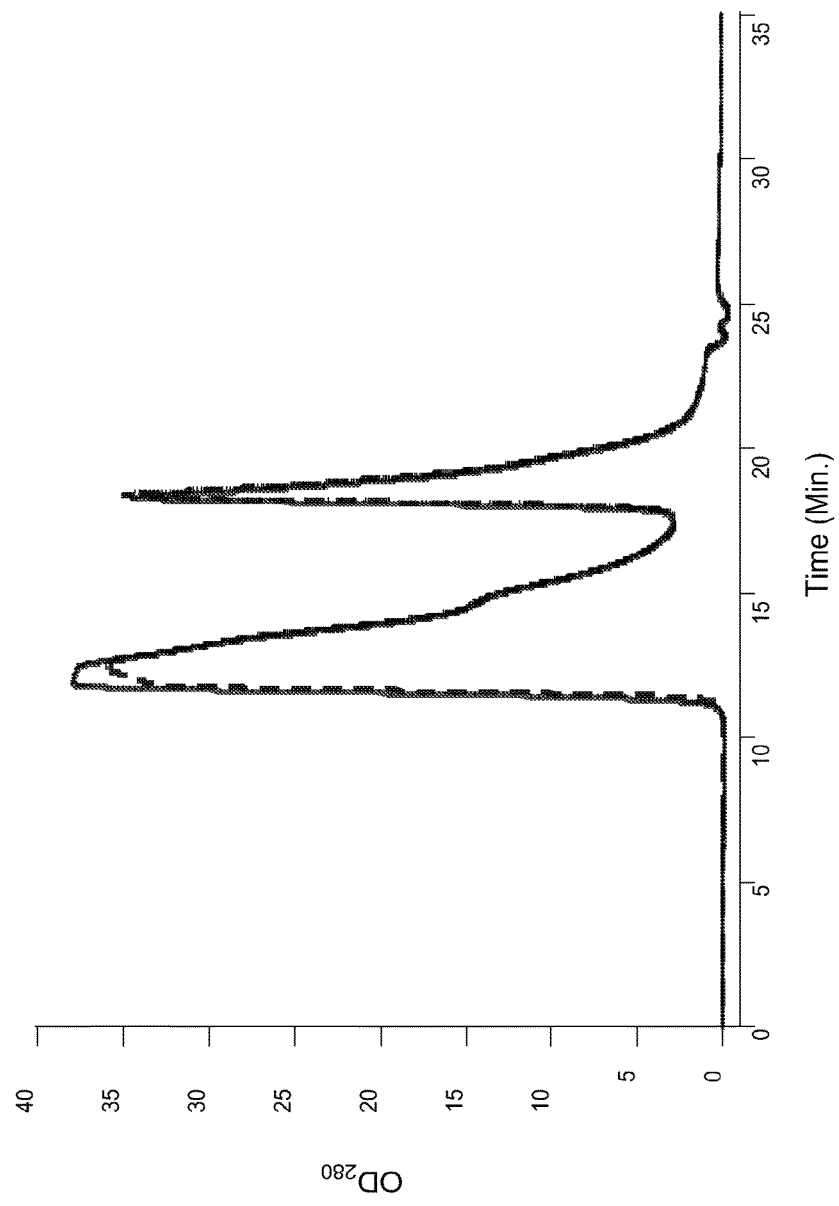
FIG. 2 shows a comparison between the mixture of IgG and Protein G stored at ambient temperature for 44 h (solid line), and the same mixture agitated for 44 h at ambient temperature (dashed line).

Effect of agitation of protein A and protein G complexes of IgG. The prior Example 1 is repeated, subjecting the IgG+Protein A or IgG+Protein G to agitation on a shaker at room temperature for 44 h. Examination by HP-SEC demonstrates that IgG again forms complexes with Protein A and Protein G, and that little increase in aggregate formation has occurred, thus demonstrating suppression of aggregation of IgG (see FIGS. 1 and 2).

Example 3

Effect of agitation of protein A and protein G complexes of IgG, analysis by UV. Samples of fresh IgG, fresh IgG+ Protein A, and fresh IgG+Protein G are subjected to agitation on a shaker at room temperature for 44 hours. A sample of fresh IgG is held at room temperature for 44 h without agitation as a control. The samples are then examined by UV spectroscopy, recording the spectra between 240 and 400 nm using an Agilent 8453 UV-Vis spectrophotometer. Increased UV absorbance at 350 nm has been associated with the presence of IgG aggregates in solution and an "aggregation index" based on UV Absorbance can be measured. The aggregation index (A.I.) is determined in triplicate from the UV spectra using the equation $A.I.=OD_{350}/(OD_{280}-OD_{350})\times 100$. The spectra suggest that aggregates are formed in the IgG sample, that some suppression of aggregation has occurred in the IgG+Protein G sample, and that considerable suppression of aggregation has occurred in the IgG+Protein A sample. Further, the A.I. values for the agitated IgG sample are significantly greater than those for the IgG+ Protein A sample and the non-agitated control, suggesting significant suppression of aggregation in the IgG+Protein A sample.

Example 4

Effect of agitation of protein A and protein G complexes of IgG, analysis by Dynamic Light Scattering (DLS). Samples of fresh IgG, fresh IgG+Protein A, and fresh IgG+Protein G with agitation on a shaker at room temperature for 44 hours. The samples are then examined with DLS, using a Zetasizer Nano ZS90 (Malvern Instruments, Ltd., Westborough Mass.). Non-stressed and stressed IgG samples (1 mL) with Protein A-free beads or without beads are diluted to 1.98 mL with PBS prior to analysis. The absorbance is measured in polystryrene cuvettes (VWR, West Chester, USA) with a path length of 10 mm at 25° C. Each sample is recorded 3 times with 7 sub-runs of 10 s. The Z-average diameter is calculated using the Dispersion Technology Software (Ver. 4.20, Malvern). All values are determined in triplicate and the errors reported as standard deviations. The results indicate that agitation significantly increases the Z-average diameter for samples without Protein A, corresponding to the formation of large aggregates. However, the Z-average diameter of IgG samples agitated with Protein A only increased to 39 nm, consistent with prevention of aggregation, as shown in the tables below.

TABLE 1A

|  | A.I. average | SE |
| --- | --- | --- |
| IgG RT 44 h | 0.1 | 0.0 |
| IgG + Protein G RT 44 h | 0.9 | 0.1 |
| IgG + Protein A RT 44 h | 0.6 | 0.1 |
| IgG agitation 44 h | 49.2 |  |
| IgG + ProteinG agitation 44 h | 43.7 | 3.2 |
| IgG + ProteinA agitation 44 h | 2.1 | 0.4 |

TABLE 1B

|  | Z-average size | SE |
| --- | --- | --- |
| IgG + Protein G RT 44 h | 51 | 1 |
| IgG + Protein A RT 44 h | 26 | 1 |
| IgG agitation 44 h | 2327 | 113 |
| IgG + ProteinG agitation 44 h | 2519 | 182 |
| IgG + ProteinA agitation 44 h | 39 | 2 |

Example 5

Protein concentration determination and SDS-PAGE. To quantify large insoluble aggregates, protein concentrations are determined in triplicate by the Bradford method (Bio-Rad DC, Bio-Rad Laboratories, Hercules, Calif.) before and after centrifugation at 14,000 rpm for 10 min, using BSA as a standard. The percentage of large insoluble aggregates is determined as the difference between protein concentrations in the centrifuged and un-centrifuged samples. Aggregate formation is also evaluated by applying samples to a 4-15% Tris HCl gradient gel using a broad range molecular weight marker (Bio-Rad Laboratories). All the samples are spun down at 14,000 rpm for 10 min; the precipitate is resuspended, applied to 5.times. SDS protein loading buffer with or without reducing agent, and heated at 95° C. for 5 min, then subjected to SDS-PAGE. The results indicate that samples agitated without Protein A show opalescence or visible precipitates. A band of high molecular weight aggregates is also noted at the top of the stacking gel under non-reducing conditions for these samples.

Example 6

Bis-ANS Fluorescence Label Study. 1 mg/mL IgG samples are diluted to 0.1 mg/mL in PBS. 20 .mu.L of a 100 .mu.M Bis-ANS solution (2 mM Bis-ANS stock solution diluted with PBS) is added to 1.98 mL of 0.1 mg/mL IgG samples. The samples are excited at 385 nm (slit width, 3 nm), and the emission is recorded from 410 to 600 nm (slit width 3 nm) using an average of 10 scans for each spectrum. All the spectra are corrected by subtracting the emission spectrum of the buffer dye solution. In agitated samples without Protein A, the fluorescence emission spectra of Bis-ANS show increased intensity and a blue shift of ~20 nm relative to un-agitated samples, suggesting increased exposure of hydrophobic surfaces as a result of aggregation. Fluorescence intensity of IgG agitated with Protein A is similar to unstressed sample, suggesting the prevention of aggregation.

Example 7

IgG Stabilization on a Protein G Resin. As described herein, therapeutic proteins may be stabilized when bound to immobilized ligands. A commercially available mixed IgG from human serum (Cat. no. 14506, Sigma-Aldrich, St. Louis, Mo.) and Protein G agarose beads (Cat. no. 20398, Pierce Chemical Co., Rockford, Ill.) are used. An IgG solution is prepared (1 mg/mL in 50 mM $K_2HPO_4/KH_2PO_4$, pH 7.3) and filtered (0.45 .mu.m) to remove any initial aggregates or suspended solids. UV absorbance after 1 h incubation verifies that the IgG binds Protein G beads but does not bind appreciably to control agarose beads.

Example 8

Samples from the previous Example 7 are agitated to promote aggregation of the IgG and to assess the ability of Protein G binding to prevent aggregation. Solution samples containing IgG (1 mL; 1 mg IgG/mL in 2 mL microcentrifuge tube) and Protein G beads (Table 2, #3) or control beads (i.e., agarose beads without Protein G; Table 2, #4) were placed vertically on a platform shaker and shaken at 1200 rpm for 24 h. Samples containing beads were then spun down (500 g, 1 min), the supernatant collected and the Protein G beads washed with buffer (3.times.). The IgG bound to Protein G beads was then eluted with glycine buffer (0.1 M, pH 2.5) and neutralized (1 M $K_2HPO_4$, pH 10.0); these solutions are referred to as "eluate". Samples showing opalescence or visible precipitates were centrifuged (18,000 g, 10 min); the resuspended solids are referred to as "precipitate". An IgG solution kept at room temperature for 24 hours without agitation (Table 2, #1) and an IgG solution subjected to agitation without beads (Table 2, #2) were included as controls.

TABLE 2

Aggregation of IgG Stored with Protein G Agarose Beads[a]

| # | Sample Description | Native Protein, % | Soluble Aggregate, % | Insoluble Aggregate, % | Total Aggregate, % |
| --- | --- | --- | --- | --- | --- |
| 1 | IgG | 95.9 + 0.4 | 4.1 + 0.4 | NDd | 4.1 + 0.4 |
| 2 | IgG + Shaking | 85.8 + 0.1 | 8.2 + 0.2 | 6.0 + 1.0 | 14.2 + 1.5 |
| 3 | IgG + Protein G Beads + Shaking Eluate[b] | 94.1 + 0.4 | 5.9 + 0.4 | ND | 5.9 + 0.4 |
| 4 | IgG + Control Beads + Shaking Supernatant[c] | 86.0 + 1.2 | 8.1 + 0.5 | 5.9 + 1.7 | 14.0 + 1.2 |

[a]Following 24 h storage with and without shaking; see Table 1 for conditions; n ≥ 5 ± SD;
[b]15 Eluate recovered after storage and treatment with release agent (Gly buffer; see text),
[c]Supernatant recovered after storage and centrifugation at 500 g,
dND = not detected.

Protein G was stored with 90 μL Protein G agarose beads; Control was stored with 90 μL control agarose beads; and spinning was at 1200 rpm on a platform shaker.

Samples were analyzed by UV-Vis and fluorescence spectroscopy, SDS-PAGE and HP-SEC to assess agitation-induced aggregation. UV-Vis spectra were recorded from 200 to 400 nm before and after centrifugation at 18,000 g for 10 min. To quantify large insoluble aggregates, protein concentrations were determined in triplicate by the Bradford method (Bio-Rad DC, Bio-Rad Laboratories, Hercules, USA) using bovine serum albumin as a standard, before and after centrifugation (18,000 g, 10 min). Aggregation was also evaluated by applying control and stressed IgG samples to a 4-15% Tris-HCl gradient SDS-PAGE gel (Bio-Rad Laboratories, Hercules, USA) using a broad range molecular weight marker. To assess formation of soluble aggregates, samples were first centrifuged to remove insoluble aggregates (18,000 g, 5 min) and the supernatant analyzed by HP-SEC as described previously (Agilent 1200 system; Tosoh TSK Gel 3000 SWXL column; 0.5 mL/min; mobile phase 50 mM $K_2HPO_4/KH_2PO_4$, 100 mM $Na_2SO_4$, pH 7.1; UV detection at 280 nm). Fluorescence emission spectra were recorded in the presence of 1 .mu.M Bis-ANS (Fluoromax-3 Fluorometer, Horiba Jobin Yvon Inc., NJ; excitation 385 nm, emission 410 to 600 nm; slit width 3 nm; 10 scans per spectrum).

The results show that IgG aggregation is reduced when the protein is bound to Protein G agarose beads. UV spectra showed increased absorbance at 350 nm for IgG samples without Protein G beads or containing control beads, which may be consistent with the formation of aggregates. Opalescence was also noted on visual inspection of these samples. In contrast, samples stored with Protein G beads showed lower absorbance at 350 nm that was similar to unstressed samples. SDS-PAGE showed the absence of high molecular weight species for protein eluted from Protein G beads after shaking, though these species may be evident in samples shaken without beads or with control beads. HP-SEC shows a soluble dimer for all samples. The peak for samples stored with Protein G beads (IgG+Protein G+shaking) is similar to that for unstressed samples (IgG RT), and less than for agitated controls (IgG+shaking, IgG+control+shaking). Fluorescence emission spectra in the presence of Bis-ANS showed decreased intensity for samples containing Protein G beads, which may be consistent with lower levels of soluble and suspended aggregates. Quantitative estimates of % monomer, % soluble aggregate (both by SEC) and % insoluble aggregate (by protein concentration determination before and after centrifugation) show decreases in aggregated species for samples containing Protein G (Table 2, #3) compared with agitated samples containing control beads (Table 2, #4) or without beads (Table 2, #2).

Example 9

Identifying Peptide Epitopes with Affinity for IgG. Peptide epitopes with high affinity for IgG may be derived readily from combinatorial libraries and proteolytic digests of protein mixtures. Proteolytic digests of Protein G were immobilized on POROS-Aldehyde resin by Schiff base coupling at their N-termini and the peptides screened for their ability to bind IgG from human plasma. The peptides TVTEKPEV (SEQ ID NO: 12) and TVTEKVIDASELTPAVT (SEQ ID NO: 5) bound IgG with selectivity comparable to Protein A. The binding constant of TVTEKPEV (SEQ ID NO: 12) for human IgG was in the $10^6$ range by HPLC methods. Selectivity of the POROS-TVTEKPEV (SEQ ID NO: 12) sorbent for human IgG was greater than for rabbit, goat, or mouse IgG. In all, four peptides showing high affinity for IgG were isolated from protein G digests by this method. Similar peptides with high affinity for human IgG were also isolated and characterized from cytochrome c (CAQCHTVEK) (SEQ ID NO: 6) and mouse anti-human polyclonal IgG digests (GAQGHVVEK) (SEQ ID NO: 7) using this method. Elution of IgG from immobilized peptide columns was achieved with ionic strength gradients, which may indicate that IgG binds predominantly by electrostatic complementarity. Without being bound by theory, it is believed herein that because ethylene glycol assists elution, some hydrophobic effects may also be involved.

Example 10

Studies Demonstrating Synthesis of Polyaspartamide (PAA) with Pendant Peptides. The stability of an IgG bound to polyaspartamide (PAA) with pendant peptide epitopes derived from Protein G is tested. The ability to synthesize hybrid PAA polymers and to immobilize the polymers on glass supports is demonstrated.

PAA and related derivatives have been reported to compose a group of protein-like polymers that have been grafted to produce drug delivery systems and are non-immunogenic, biocompatible and biodegradable (see, for example, Yang et al., Histidine-conjugated poly(amino acid) derivatives for the novel endosomolytic delivery carrier of doxorubicin, J Controlled Rel 114:60-68 (2006); Peng et al., Synthesis and characterization of poly-.alpha.,.beta.-[N-(2-hydroxyethyl)-L-aspartamide]-g-poly(glycolide) amphiphilic graft copolymers as potential drug carriers, Colloid Polym Sci 284:834-842 (2006); Kang et al., Self-aggregates of poly(2-hydroxyethyl aspartamide) copolymers loaded with methotrexate by physical and chemical entrapments, J Controlled Rel 81(1-2):135-144 (2002); Pitarresi et al., A new biodegradable and biocompatible hydrogel with polyamino-acid structure, Int J Pharmaceutics 335(1-2):130-137 (2007); Cao et al., Preparation a novel pH-sensitive blend hydrogel based on polyaspartic acid and ethylcellulose for controlled release of naproxen sodium. J Appl Polym Sci 113(1):327-336 (2009)). PAA was synthesized from polysuccinimide (PSI) using conventional processes. PSI was prepared in 96% yield by refluxing DL-aspartic acid (50 g) and phosphoric acid (2.166 g) in N-methyl-2-pyrrolidinone (NMP) (48 g) and 1,3,5-trimethylbenzene (112 g) at 165-170° C. for a day. The solid product was crushed in water, washed multiple times with methanol, vacuum dried, and dissolved in hot DMF at 50° C. NMR analysis, SEC and MALDI showed that the PSI product was a linear polymer of approximately 25 kD, in agreement with literature reports.

When dissolved in DMF, primary amines are known to readily derivatize PSI through nucleophilic addition. PSI (100 mg) was dissolved in DMF (1 mL) and a mixture of peptides added at a 1:5 molar ratio for each peptide (i.e., TVTEKPEV (SEQ ID NO: 12), GAQGHVVEK (SEQ ID NO: 7) and three proprietary peptides). After 24 h incubation at 50° C., enthanolamine was added to a final concentration of 5%, with incubation for another 12 h. The product was isolated by aqueous extraction. PAA derivatized with ~5 conjugated peptides of the same sequence and with ethanol amine had a MW ~45 kD according to SEC. Derivatization with 5 different peptides gave MW ~50 kD. The product is hydrophilic and water soluble. Since the succinimide group of PSI is known to react readily with amines, PSI is believed to readily bind to silyl amine modified glass. Peptides and proteins are immobilized on the PSI derivatized support via residual succinimide groups using conventional reagents and processes.

Example 11

Stabilization of IgG in solution and in dry solids using commercial Protein G affinity chromatography resins as a model system. An IgG1 was selected as a representative of this drug class. A hybridoma cell line, HB-8177, producing a human IgG1 monoclonal antibody against tetanus toxin is obtained from ATCC (Rockville, Md.), grown following the manufacturer's instructions and established protocols, and purified with Protein G affinity chromatography using an AKTA FPLC system (GE Healthcare Bio-Sciences Corp, Piscataway, N.J.). The protein is stabilized using Protein G agarose beads (see 2.3.1.1) or other commercial immobilized Protein G affinity resin.

Example 12

Sample preparation and characterization. Samples are prepared as IgG solutions at low concentration (1 mg/mL), at high concentration (50 mg/mL) and as lyophilized solids. Each is modified by the addition of Protein G beads, control beads or remain unmodified. The study design thus includes nine (3.times.3) sample types. High concentration formulations are included because the desired doses of therapeutic IgGs are believed to increasingly require this, with attendant increases in aggregation propensity. Dry solid formulations are also described. Lyophilized samples are prepared using a programmable lyophilizer and methods routine in the PI's labs. IgG binding to Protein G beads are confirmed using UV spectroscopy. IgG conformation in solution and on the bead support is assessed using FTIR to monitor shifts in .beta.-sheet bands. Melting curves are used to assess changes in thermal stability induced by binding, via annealing temperature (Tm).

Sample storage. Solution samples are stored in sealed vials: (a) at room temperature without agitation, (b) at room temperature with agitation and (c) at 50° C. without agitation. These storage conditions introduce mechanical stress (b) or thermal stress (c) and have been shown to promote IgG aggregation (see, for example, Serno et al., Inhibition of agitation-induced aggregation of an IgG-antibody by hydroxypropyl-.beta.-cyclodextrin, J Pharm Sci 99(3):1993-1206 (2010)). Solid samples are stored in open vials at 50° C. with relative humidity (RH) controlled to desiccated (~0% RH), low (~30% RH) and high (~75% RH) levels established using desiccants or saturated salt solutions. The use of open vials for solid samples is believed to allow equilibration of water activity in solid and vapor phases.

Sample analysis to monitor IgG degradation. Samples are removed from storage at selected times and analyzed to quantify physical and chemical degradation products. Without being bound by theory, it is believed that aggregation is the dominant route of degradation. Aggregate formation is monitored using RP-SEC, SDS-PAGE, UV-Vis spectroscopy and Bis-ANS binding. Chemical degradation is checked using IEC, a method routinely used to identify charge variants produced via deamidation. Tryptic mapping of light and heavy chains with LC/MS analysis is used to detect oxidation products, clipping variants and changes in glycosylation.

Data analysis. Data from the stability studies relates the amount of degradant (e.g., soluble aggregate, insoluble aggregate, charge variant, etc.) to storage time for the nine sample types. Within each sample type, data is analyzed using nonlinear regression to establish apparent reaction order and generate degradation rate constants. ANOVA is then used to compare degradation rates and extents of degradation at selected time points among the sample types, testing the null hypothesis that all formulations provide identical IgG stabilization. A power calculation to establish the number of samples needed per group (n) (one-way ANOVA, nine groups, SD=0.5%) indicates that differences in percent aggregation of 1.5% are detectable with power>0.95 for n=6. Therefore, n=6 is used for each sample type.

Example 13

Synthesis of polyaspartamide polymers with pendant peptide epitopes derived from Protein G and use for stabilizing IgG in solution and in dry solids. PAA with a single pendant peptide (TVTEKPEV) and with multiple peptide epitopes identified by screening are prepared. The pseudo-ligands are characterized and evaluated for their ability to stabilize IgG using methods similar to those in above. Immobilized pseudo-ligands are also evaluated.

Synthesis of PAA with pendant peptide epitopes. PAA with pendant TVTEKPEV (SEQ ID NO: 12) peptides is synthesized and the ability of this hybrid polymer to bind and stabilize the IgG1 is evaluated. TVTEKPEV (SEQ ID NO: 12) and other synthetic peptides are purchased from commercial sources (e.g., American Peptide Co., Sunnyvale, Calif.). TVTEKPEV (SEQ ID NO: 12) is believed to demonstrate high affinity binding to human IgG (see 2.3.1.2) and it has been successfully conjugated it to PAA. While TVTEKPEV (SEQ ID NO: 12) is believed to have few labile amino acids, without being bound by theory, it is possible that its Lys side chain may react with PSI during production of the pseudo-ligand, reducing binding affinity to IgG. To avoid this, the peptide is purchased in Lys-protected form (e.g., Fmoc) and deprotected following polymer synthesis. As controls, PAA derivatized with a sequence-scrambled form of TVTEKPEV (SEQ ID NO: 12) (to a degree of substitution comparable to the pseudo-ligand) is synthesized, as well as peptide-free PAA.

Pseudo-ligands are synthesized having more than one type of pendant peptide. The use of multiple peptides is believed to generate higher binding affinity through cooperative effects. Without being bound by theory, the binding interaction is envisioned to occur much like protein folding, involving high levels of ligand cooperativity and conformational compliance within the PAA. Three to five peptides that bind Fc-IgG and show low sequence homology (which may be suggestive of distinct binding sites) are identified using the methods described above, and then conjugated to PAA. Alternatively, the peptides are selected from previous literature reports (e.g., HWRGWV (SEQ ID NO: 8)) and used together with TVTEKPEV (SEQ ID NO: 12). Polymers that are peptide-free or are derivatized with scrambled forms of the peptides are synthesized as controls.

Characterization of PAA polymers synthesized. PAA derivatives are characterized by $^1$H NMR to confirm structure and by SEC to determined average molecular weight and polydispersity. Polymer binding to IgG is evaluated using a Biacore system (Biacore 3000, GE Healthcare), with immobilization of the IgG on the carboxymethylated support (Biacore C1 chip) and the polymer in solution. Binding affinity (KD), association (ka) and dissociation (kd) rate constants, and possible cooperativity in binding are determined by analysis of the biosensograms using the supplied software. The ability of the free peptide (i.e., TVTEKPEV (SEQ ID NO: 12), mixed peptides) to release of the IgG from the pseudo-ligand complex is evaluated in Biacore studies by including peptides in solution.

Preparation and characterization of immobilized pseudo-ligands. Immobilized forms of the pseudo-ligands from single peptide studies and multiple peptide studies are prepared using the methods described herein. Without being bound by theory, it may be that relatively high concentrations of PSI are advantageous to produce a "brush-like" immobilization, so that flexible domains are available for peptide derivatization and IgG binding.

The following publications, and each additional publication cited herein, are incorporated herein by reference:

Sanchez-Ruiz et al., Ligand effects on protein thermodynamic stability, Biophysical Chemistry 126:43-49 (2007)

Zhao & Topp, Recent U.S. patents on protein drug formulation: 2000-2007, Recent Patents on Drug Delivery & Formulation 2/3:200-208 (2008)

Gadgil, Solid-state protein formulation. In USPTO, editor, ed., United States: Amgen, Inc. p 74 (2007)

Jindal et al., High speed, automated, continuous flow, multi-dimensional molecular selection and analysis. ed., United States: PerSeptive Biosystems, Inc. (2002)

Yang et al., Hexamer peptide affinity resins that bind the Fc region of human immunoglobulin G, J Peptide Res, 2006, 66 (Suppl 1), 120-137 66(Suppl. 1):120-137 (2006)

The invention claimed is:

1. A pharmaceutical composition suitable for delivery to a patient comprising:
   a mixed human IgG having an Fc domain; and
   a protein A fragment consisting of sequences selected from the group consisting of FNKEQQNAFYEIL (SEQ ID NO:3) and EQRNGFIQSLKD (SEQ ID NO:4), wherein the mixed human IgG is bound to the protein A fragment via the Fc domain and is substantially free of IgG aggregates, wherein the ratio of mixed human IgG to the protein A fragment is approximately 1:4.

2. A pharmaceutical composition comprising:
   a protein drug having an Fc domain; and
   a polyamino acid ligand consisting of FNKEQQNAFYEIL (SEQ ID NO:3), or a polyamino acid ligand consisting of EQRNGFIQSLKD (SEQ ID NO:4), wherein the ratio of the protein drug to the polyamino acid ligand is approximately 1:4 wherein the polyamino acid ligand is bound to the Fc domain of the protein drug and the protein drug exhibits reduced aggregation as compared to the protein drug alone.

3. The pharmaceutical composition comprising of claim 2, wherein the pharmaceutical composition is a solution.

4. The pharmaceutical composition comprising of claim 2, wherein the protein drug is mixed human IgG.

5. The pharmaceutical composition comprising of claim 2, wherein the protein drug is IgG1, IgG2 or an immunoglobulin G-like protein.

6. The pharmaceutical composition comprising of claim 2, wherein the polyamino acid ligand is non-immunogenic.

7. A pharmaceutical composition comprising:
   a protein drug having an Fc domain; and
   a polypeptide consisting of 13 to 50 amino acids that comprises a polyamino acid ligand consisting of FNKEQQNAFYEIL (SEQ ID NO:3),
   wherein the ratio of the protein drug to the polyamino acid ligand is approximately 1:4, wherein the polyamino acid ligand is bound to the Fc domain of the protein drug, and wherein the protein drug exhibits reduced aggregation as compared to the protein drug alone.

8. A pharmaceutical composition comprising:
a protein drug having an Fc domain; and
a polypeptide consisting of 12 to 50 amino acids that comprises a polyamino acid ligand consisting of EQRNGFIQSLKD (SEQ ID NO:4),
wherein the ratio of the protein drug to the polyamino acid ligand is approximately 1:4, wherein the polyamino acid ligand is bound to the Fc domain of the protein drug, and wherein the protein drug exhibits reduced aggregation as compared to the protein drug alone.

9. A method of stabilizing a protein drug, the method comprising:
contacting a free protein drug having an Fc domain with a free polyamino acid ligand that binds to the Fc domain, wherein the ratio of protein drug to the polyamino acid ligand is approximately 1:4, thereby creating a stabilized protein drug exhibiting a reduced formation of aggregates as compared to the free protein drug, wherein said polyamino acid ligand consists of sequences selected from the group consisting of SEQ ID NO:3 and SEQ ID NO:4.

10. The method of claim 9, wherein the protein drug is mixed human IgG, IgG1, IgG2 or an immunoglobulin G-like protein.

11. A method of stabilizing a protein drug, the method comprising:
contacting a free protein drug having an Fc domain with a free polypeptide consisting of 13 to 50 amino acids that comprises a polyamino acid ligand consisting of FNKEQQNAFYEIL (SEQ ID NO:3), or
contacting a free protein drug having an Fc domain with a free polypeptide consisting of 12 to 50 amino acids that comprises a polyamino acid ligand consisting of EQRNGFIQSLKD (SEQ ID NO:4),
wherein the polyamino acid ligand binds to the Fc domain, and wherein the ratio of protein drug to the polyamino acid ligand is approximately 1:4, thereby creating a stabilized protein drug exhibiting a reduced formation of aggregates as compared to the free protein drug alone.

12. The method of claim 11, further comprising contacting the stabilized protein drug with a releasing agent, the releasing agent causing the polyamino acid ligand to disassociate from the Fc domain.

13. The method of claim 12, where the releasing agent comprises glycine, a competitive ligand for the polyamino acid ligand, an acid, or an acidic buffer.

14. The method of claim 9, further comprising agitating the stabilized protein drug, wherein the stabilized protein drug remains substantially free of aggregates following the agitating.

15. The method of claim 14, wherein the agitating comprising shaking for at least 24 hours.

16. The method of claim 14, wherein at least 50% of the stabilized protein drug is soluble protein following the agitating.

17. The method of claim 16, wherein at least 90% of the stabilized protein drug is soluble protein following the agitating.

18. A pharmaceutical composition suitable for long term storage comprising:
a protein drug having an Fc domain; and
a polyamino acid ligand comprising an epitope sequence of FNKEQQNAFYEIL (SEQ ID NO:3), or a polyamino acid ligand comprising an epitope sequence of EQRNGFIQSLKD (SEQ ID NO:4), wherein the polyamino acid ligand is further releasably embedded in a polymer backbone and bound to the Fc domain of the protein drug.

19. The pharmaceutical composition according to claim 18, wherein the polymer backbone is a polyalkylene glyocol or a polyoxyalkylene.

20. The pharmaceutical composition according to claim 18 further comprising an stabilizing excipient on a solid surface to immobilize the polyamino acid ligand bound protein drug, wherein said stabilizing excipient covalently binds to the polyamino acid ligand.

* * * * *